United States Patent [19]

Samuelsen

[11] Patent Number: 5,486,158
[45] Date of Patent: Jan. 23, 1996

[54] GROOVED HYDROCOLLOIDAL DRESSING

[75] Inventor: Peter B. Samuelsen, Rungsted Kyst, Denmark

[73] Assignee: Coloplast A/S, Denmark

[21] Appl. No.: 167,983

[22] PCT Filed: Jun. 23, 1992

[86] PCT No.: PCT/DK92/00197

§ 371 Date: Jan. 10, 1994

§ 102(e) Date: Jan. 10, 1994

[87] PCT Pub. No.: WO93/00056

PCT Pub. Date: Jan. 7, 1993

[30] Foreign Application Priority Data

Jun. 24, 1991 [DK] Denmark ................................ 1227/91

[51] Int. Cl.⁶ ........................................................ A61F 13/00
[52] U.S. Cl. .................................. 602/46; 602/43; 602/52; 602/54
[58] Field of Search ...................... 602/41, 42, 43, 602/46, 52, 56, 58, 60, 54; 604/336

[56] References Cited

U.S. PATENT DOCUMENTS

| | | | |
|---|---|---|---|
| 3,339,546 | 9/1967 | Chen | 128/156 |
| 3,674,027 | 7/1972 | Fleischmajer | 128/268 |
| 4,214,582 | 7/1980 | Patel | 128/156 |
| 4,612,230 | 9/1986 | Liland et al. | 428/167 |
| 4,699,134 | 10/1987 | Samuelsen | 128/156 |
| 4,867,748 | 9/1989 | Samuelsen | 604/336 |
| 5,012,801 | 5/1992 | Feret | 128/155 |
| 5,115,801 | 5/1992 | Cartmell et al. | 602/48 |
| 5,250,043 | 10/1993 | Castellana et al. | 604/336 |
| 5,356,372 | 10/1994 | Donovan et al. | 602/58 |

FOREIGN PATENT DOCUMENTS

| | | |
|---|---|---|
| 0164319 | 12/1985 | European Pat. Off. . |
| 0230373 | 7/1987 | European Pat. Off. . |
| 0264299 | 4/1988 | European Pat. Off. . |

*Primary Examiner*—Corrine M. Maglione
*Assistant Examiner*—Michael L. Arness
*Attorney, Agent, or Firm*—Ostrolenk, Faber, Gerb & Soffen

[57] ABSTRACT

A skin-friendly dressing which has a high moisture absorbing capacity, a high degree of flexibility and good integrity. The dressing includes a moisture-absorbing adhesive sheet to be adhered to the skin and mucous membranes, with a layer of water swellable colloid which is dispersed in or mixed with a water insoluble viscous elastomer binder and, if desired, usual auxiliary materials. The adhesive sheet at one outwardly directed surface is firmly connected to a non-adhesive water impervious cover layer, and at the other, against-the-skin or mucous-membrane directed surface of the adhesive sheet, a removable protecting sheet. The adhesive sheet is provided with one or several grooves or ditches that fully or partly surround a central part of the adhesive sheet.

14 Claims, 2 Drawing Sheets

GROOVED HYDROCOLLOIDAL DRESSING

BACKGROUND OF THE INVENTION

1. Field of the Invention

The present invention refers to a skin-friendly bandage or dressing for covering wounds, burns or similar damages of the human skin, or ostomi openings.

2. Description of the Related Art

From U.S. Pat. No. 4,867,748 is known a skin-friendly dressing comprising a water soluble or water swellable hydrocolloid, a water-insoluble, viscous elastomeric binder and optionally also a tackifying resin. This known dressing is formed as a sealing pad having bevelled outer edges and optionally also, if annular, a bevelled inner edge.

From EP Patent Application No. 164 319 is known a pressure relieving bandage comprising a pressure-sensitive adhesive layer containing a hydrocolloid, a foam layer provided with cuts dividing the foam layer, into sections, and a film layer between the adhesive layer and the foam layer. Because of the cuts in the foam layer, it is possible to remove one or more foam sections without damaging the bandage.

The dressings described in this and other similar patents are rather stiff as they must have a considerable thickness in order to contain a sufficient amount of moisture absorbing materials.

SUMMARY OF THE INVENTION

An object of the present invention is to provide a bandage or wound dressing having a high moisture absorbing capacity and simultaneously a high degree of flexibility for covering surface areas or the human body.

It is also an object of the invention to provide a bandage or wound dressing comprising a medicament or a similar physiologically active material that may be transferred to the skin or mucous membranes to which the bandage or dressing is adhered.

According to the invention, it has been found that a surprisingly high degree of flexibility may be obtained without compromising the integrity and the absorbing properties when the bandage or wound dressing is provided with grooves or ditches.

The skin-friendly bandage or dressing according to the invention comprises a moisture absorbing, to skin and mucous membranes adhering adhesive sheet, consisting of a layer of a water swellable colloid which is dispersed in or mixed with a water insoluble viscous elastomer binder and, if desired, usual auxiliary materials, the adhesive sheet at one outwardly directed surface being firmly connected to a non-adhesive water impervious cover layer, and the other against the skin or mucous membrane directed adhesive surface being provided with a removable protecting sheet. The bandage or wound dressing is specificly characterized in that the adhesive sheet is provided with one or several grooves or ditches that fully or partly surround the central part of the adhesive sheet and that the cover layer follows the contour or the outwardly directed surface of one or several grooves or ditches.

The swellable colloid particles preferably consist of one or more water soluble or water swellable hydrocolloid polymers or gums. Suitable examples are carboxymethylcellulose, dextran, pectin, guar gum and polyvinylalcohol. Further examples of such materials are mentioned in U.S. Pat. No. 4,867,748, EP 0 122 344.

The elastomer binder, acting as a medium for dispersing the hydrocolloid particles, is any known water-insoluble elastomeric substance, preferably a polymer or copolymer. Suitable examples are polyisobutylene, silicone rubber, acrylonitride rubber, polyurethane etc. Further examples may be derived from the above mentioned EP 0 122 344.

If desired, any commonly used auxiliary material may be included as a component of the dressing, such as antioxidants, for example butylated hydroxyamisole or hydroxytoluene, deodorants such as chlorophyllins, or perfume agents. It is also common practice to add pharmacologically active ingredients in the adhesive composition, such as antibiotic or antimicrobial agents, such as neomycin, an antiseptic agents such as povidone iodine, and/or an antiinflammatory agent such as hydrocortisone or triamcinolone acetomide.

Further examples of such auxiliaries are enumerated in the literature, see for example EP 0 122 344, EP 0 340 945, U.S. Pat. No. 3,972,328, and U.S. Pat. No. 4,867,748.

The impervious cover layer may consist of any known useful material for the purpose. Examples of such materials are any film forming polymer, such as polyethylene, polypropylene, polyester, polyvinylchloride, polyvinylidenchloride, polyvinylacetate, polyamide, polyvinylether and polyurethane. The impervious cover layer may also be a foam, such as polyurethane foam or polyether foam.

The bandage or wound dressing may, according to an embodiment of the invention, have a hole in the central part.

The grooves or ditches may preferably have such a depth that the thickness of the sheet at the bottom of the ditch is less than ¼ of the thickness of the sheet between the ditches. The width of the grooves or ditches is up to three times the depth and, preferably, the width has the same size as the depth. A maximum of flexibility is thus obtained.

The grooves or ditches impart highly increased flexibility to the dressing.

BRIEF DESCRIPTION OF THE DRAWINGS

The invention shall be further described in connection with the drawing, where.

DETAILED DESCRIPTION OF THE PREFERRED EMBODIMENT

Figure 1:
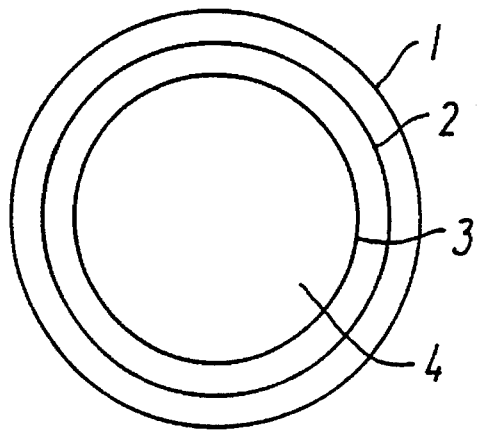
FIGS. 1, 4 and 5 are three different embodiments of the bandage according to the invention, seen from above.
Figure 2:
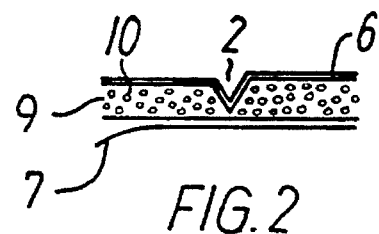
FIGS. 2, 3 and 6 illustrate various forms of grooves or ditches in the bandage.
Figure 3:
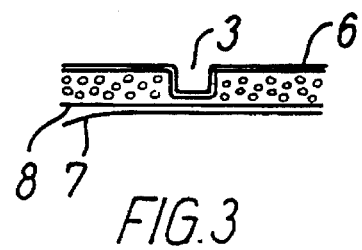
Figure 6:
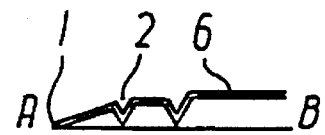

The bandage illustrated in FIG. 1 consists of a circular sheet with an outer edge 1 and two grooves 2, 3. The central part 4 has a uniform maximum thickness. As shown in FIGS. 2, 3 and 6 the grooves may have different profiles such as V- or U-shapes. An impervious cover layer 6 consisting of a polymer film or a thin foam layer is placed on top of the outer surface of layer 9 including colloid. The surface to be placed against the skin is provided with adhesive layer 8 covered by a protective removable film 7.

One or two concentric grooves improves considerably the resistance to radial swelling. This property may be measured by a method described below.

Figure 4:
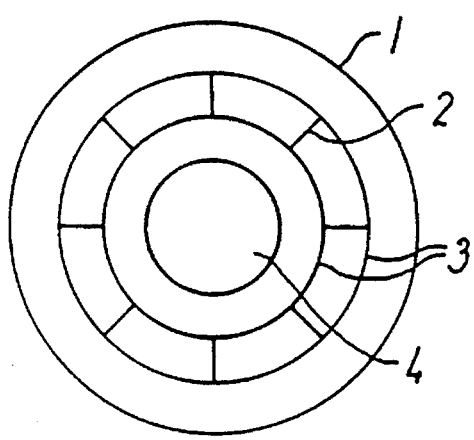

The central part 4 may be a hole as illustrated in FIG. 4.

This embodiment is suitable as bandage for ostomy openings. Increased flexibility is obtained due to concentric ditches 3 as well as radial ditches 2. Such a bandage can be rather thick having a high absorption capacity and still being highly flexible.

Figure 5:
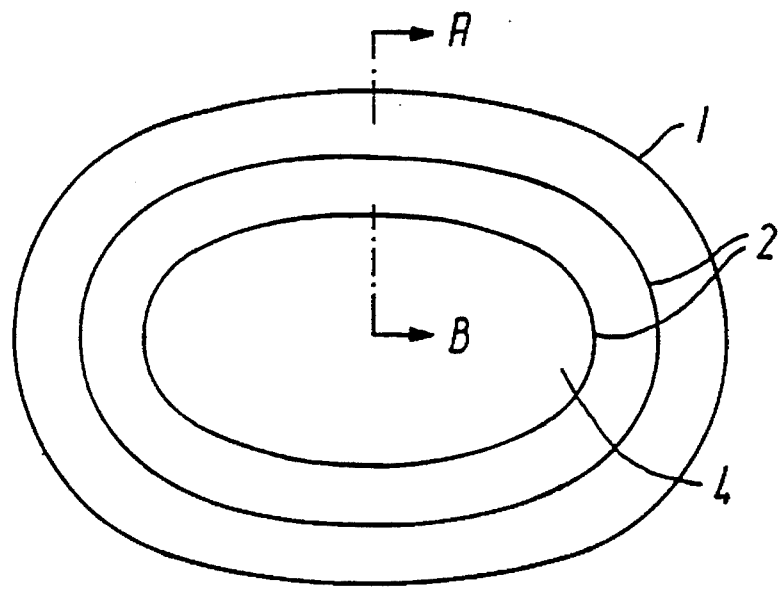
Figure 7:
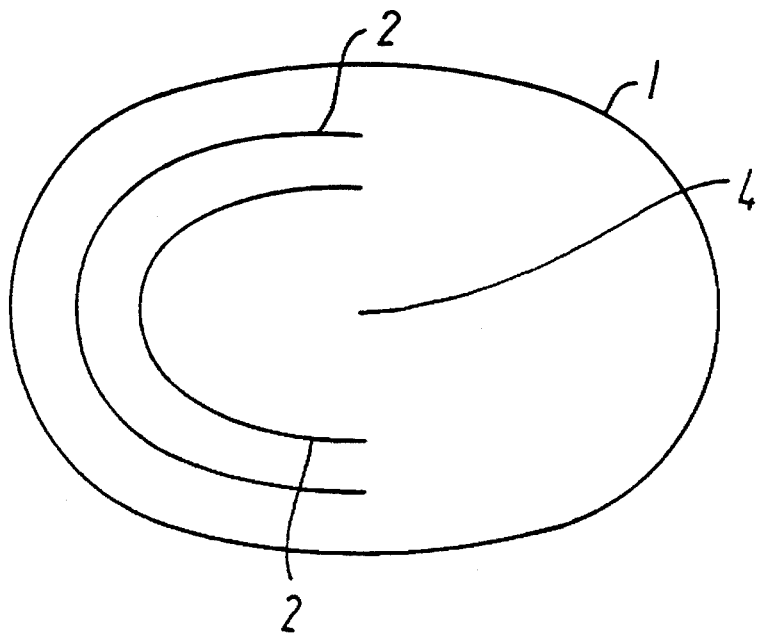
FIG. 7 illustrates a special embodiment in which only a distal part of the bandage has grooves.

The bandage shown in FIG. 5 has an elliptical outer edge 1. The bandage shown in FIG. 7 is intended to be placed a vertical surface of a body area, the distal part directed downward in order to minimize swelling in the downward direction.

The dressings according to the invention may be manufactured in various ways, e.g. by a die-casting process or a pressing process. An adequate method of manufacturing the dressing is disclosed by U.S. Pat. No. 4,867,748.

Method of Determining Radial Swelling

An apparatus of a sheet of glass (25×25 cm) with a central hole of 20 mm is connected to a reservoir of water via a tube mounted onto the said hole. At the side opposite to the tube of the sheet of glass, the product to be tested is applied with the hole as centrum. Physiological saline is introduced to the product adhering to the glass sheet by elevating the reservoir for said saline to a position above the product. A pressure of 2–10 cm of water column is applied to the product and the radially swelling from the hole out through the product may be determined. The test is performed at 37° C. and readings are taken at the times; 6 hours, 24 hours, 2, 3 and 4 days. The glass plate is placed horizontally in the test.

The invention is further illustrated by the following examples.

EXAMPLE 1

A test product from the category of hydrocolloid dressings and with a content of 40% particles of sodiumcarboxy-methyl-cellulose dispersed in an elastomeric binder consisting of polyisobutylene and covered by a polyurethane film of 30 μ was tested as a plane sheet and formed with 2 grooves as shown in FIG. 1. The grooves are concentric and centrally placed with deformation diameters of 24 mm and 34 mm.

The radial swellings at 12 hours are identical for the two dressings. However, when passing the first deformation after 24 hours a decrease in radial swelling velocity of 13% is observed for the deformed version and this decrease has after further 3 days further increased to a level of 30%.

EXAMPLE 2

A product configuration comprising the same materials as mentioned in example 1 and especially intended for leg ulcers was investigated. Here a considerable radial swelling component exists due to gravity. This means that the distal or downwardpart of a hydrocolloid dressing will swell more quickly than the rest of the product and hence give rise to product change although there may be considerable swelling capacity left in the product in total. By only deforming the distal part of the product by compartments as in the FIG. 7 and testing it by described method placing the glass sheet vertically, the period before distal leakage is improved with 18–23% when the hydrocolloid dressing is deformed compared to the identified control without deformation.

I claim:

1. A dressing having a skin-friendly moisture absorbing sheet adhering to skin and mucous membranes, the dressing comprising:

a layer of a water swellable colloid which is dispersed in or mixed with a water insoluble viscous elastomer binder, the layer having a central part, a distal, having a contour formed therein that at least partially surrounds the central part of the layer, and an opposing proximal surface;

a non-adhesive cover layer disposed on the distal surface and following the contour of the at least one groove, the cover layer being water impervious; and a removable protecting sheet, disposed on the proximal surface.

2. A dressing according to claim 1, wherein the central part is a hole.

3. A dressing according to claim 1, wherein the at least one groove is arranged concentric around the central part.

4. A dressing according to claim 1, wherein the at least one groove is arranged radially outwardly from the central part.

5. A dressing according to claim 1, wherein the at least one groove has a depth such that the thickness of the sheet at thebottom of the groove is less than ¼ of the thickness of a non-groove containing portion of the sheet.

6. A dressing according to claim 2, wherein the at least one groove has a depth such that the thickness of the sheet at the bottom of the groove is less than ¼ of the thickness of a non-groove containing portion of the sheet.

7. A dressing according to claim 3, wherein the at Least one groove has a depth such that the thickness of the sheet at the bottom of the groove is less than ¼ of the thickness of the sheet.

8. A dressing according to claim 4, wherein the at least one groove has a depth such that the thickness of the sheet at the bottom of the groove is less than ¼ thickness of a non-groove containing portion of the sheet.

9. A dressing according to claim 1, wherein the at least one groove fully surrounds the central part.

10. A dressing according to claim 9, wherein the central part is a hole and the at least one groove is arranged concentric around the hole.

11. A dressing according to claim 10, wherein the at least one groove is arranged radially outwardly from the hole.

12. A dressing according to claim 11, wherein the at least one groove has a depth such that the thickness of the sheet at the bottom of the groove is less than one quarter of the thickness of a non-groove containing portion of the sheet.

13. A dressing according to claim 1, wherein the central part is a hole and the at least one groove is arranged concentric around less than the entire circumference of the hole.

14. A dressing according to claim 13, wherein the at least one groove has a depth such that the thickness of the sheet at the bottom of the groove is less than one quarter of the thickness of a non-groove containing portion of the sheet.

* * * * *